United States Patent [19]

Tischer et al.

[11] Patent Number: 5,248,592
[45] Date of Patent: Sep. 28, 1993

[54] USE OF A DERIVATIZED ALKALINE PHOSPHATASE AS A STANDARD

[75] Inventors: Wilhelm Tischer, Peissenberg; Martin Gerber, Weilheim-Unterhausen; Hellmuth Vetter, Tutzing, all of Fed. Rep. of Germany

[73] Assignee: Boehringer Mannheim GmbH, Mannheim-Waldhof, Fed. Rep. of Germany

[21] Appl. No.: 869,863

[22] Filed: Apr. 16, 1992

Related U.S. Application Data

[63] Continuation of Ser. No. 201,523, Jun. 2, 1988, abandoned.

[30] Foreign Application Priority Data

Jun. 4, 1987 [DE] Fed. Rep. of Germany ....... 3718753

[51] Int. Cl.⁵ .................... C12Q 1/42; G01N 33/566
[52] U.S. Cl. ....................................... 435/7.4; 435/7.8; 435/21; 435/188; 435/196; 435/967; 436/827
[58] Field of Search ................. 435/7.4, 21, 188, 196, 435/967, 7.8; 436/827

[56] References Cited

U.S. PATENT DOCUMENTS 4,681,842 7/1987 Rosalki ................. 435/21
4,843,001 6/1989 Haug et al. ................. 435/28

FOREIGN PATENT DOCUMENTS 0130708 1/1985 European Pat. Off.

OTHER PUBLICATIONS

W. Behr et al., Arztl. Lab 32:159–165 (1986) (English translation).
Stowoll et al. *Advances in Carbohydrate Chemistry and Biochemistry* 37:225, 1980.
F. G. Lehmann (1980) Klin. Wochenschr. 58:947–951.
Donald W. Moss (1982) Clin. Chem. 28/10:2007–2016.
Yamamoto, K. et al. *Biochem.* 20:5894, 1981.
Onica, D. et al. *Clin. Chim. Acta* 155:285, 1986.

*Primary Examiner*—David Saunders
*Attorney, Agent, or Firm*—Felfe & Lynch

[57] ABSTRACT

Alkaline phosphatase to which is covalently bound a carbohydrate of the general formula

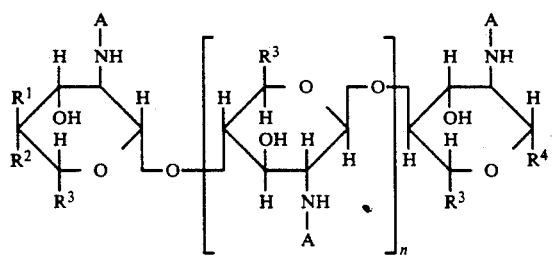

wherein n is 0, 1, 2 or 3, A is an acyl radical containing 2 to 5 carbon atoms, $R^1$ and $R^2$ are each hydrogen atoms or hydroxyl groups, $R^3$ is —COOH or —CH$_2$OH, $R^4$ is a hydroxyl group or a —CHOH—CHOH—CH$_2$OH or —NH—CO—CH$_2$—CH(NH$_2$)—COOH radical or a complex containing the carbohydrate, is used as a standard for the determination of human alkaline phosphate. Preferred carbohydrates are ovomucoid, chitobiose, chitotriose or N-acetylglucosamine-N-acetylneuraminic acid.

7 Claims, 1 Drawing Sheet

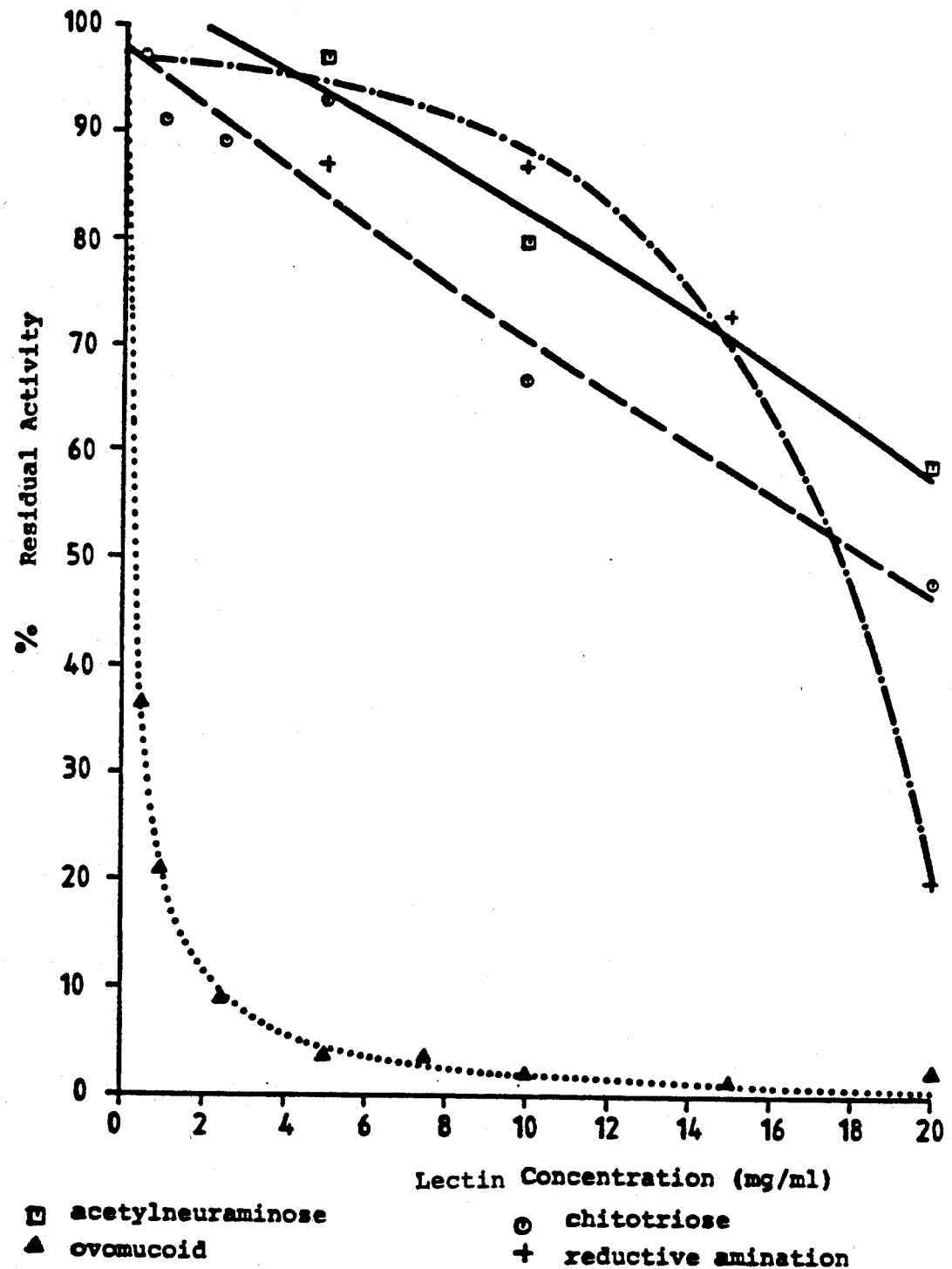

USE OF A DERIVATIZED ALKALINE PHOSPHATASE AS A STANDARD

This application is a continuation of application Ser. No. 201,523, filed Jun. 2, 1988 now abandoned.

BACKGROUND OF THE INVENTION

The present invention is concerned with the use of a derivatized alkaline phosphatase as standard for the determination of human alkaline phosphatase.

Alkaline phosphatase (EC 3.1.3.1) (AP), an enzyme which hydrolyzes the esters of phosphoric acid, is essentially formed in the body in the liver, in bones, in the kidneys, in the small intestine and, in the case of pregnant females, also in the placenta. The individual isoenzymes differ, in particular, by their carbohydrate content. In the case of diseases of the organs, in each case the isoenzyme formed in these organs passes in increased amounts into the blood circulation. Therefore, the detection of the individual enzymes in the serum is diagnostically very valuable.

As a rule, the proportion of kidney, small intestine and placenta phosphatase in the serum is small. Furthermore, small intestine and placenta phosphatase can be very easily separated from the other isoenzymes by conventional separation processes, such as chromatography. Of especial interest is the differentiation of alkaline phosphatase formed in the bones or in the liver. In this manner, there are obtained indications of carcinomas, bone disease and the type and stage of liver diseases. Therefore, in the scope of clinical diagnosis, it is important to determine not only the total concentration of alkaline phosphatase in the blood but also the proportion of the two isoenzymes.

One possibility for this purpose is provided by the different behaviour of the two isoenzymes with regard to wheat germ lectin. Whereas the alkaline bone phosphatase reacts immediately with wheat germ lectin and precipitates out, the liver phosphatase remains longer in solution and only slowly forms insoluble complexes with wheat germ lectin.

In Arztl. Lab., 32, 159-165/1986, there has been described a process for the quantitative determination of alkaline total phosphatase, as well as of alkaline bone phosphatase, in which the total content of alkaline phosphatase is first determined in a sample. Subsequently, the alkaline bone phosphatase is precipitated out with wheat germ lectin and the amount of alkaline liver phosphatase is determined in the supernatant. From these two values there can then be determined, in a simple manner, the amount of alkaline bone phosphatase.

A problem in the case of this method of determination is that no standard solutions are available. Since the determination of the amount of the alkaline bone phosphatase takes place after a precipitation reaction, for the exactitude of the determination it would be important to determine in a comparison solution, the content of the individual isoenzymes of which is known, which amount of the isoenzymes is to be found in which fraction. Therefore, for precise determinations, the provision of a standard solution is desirable.

In the case of the previously commercially available tests, for the control there is only used a phosphatase which cannot be precipitated with wheat germ lectin. This is disadvantageous since it is precisely the precipitating out of the phosphatases which contains the possibilities of error which are to be determined by testing with a standard solution. A further problem is that for the standard solution a phosphatase must be made available, the activity of which corresponds to that of the phosphatase to be detected in the blood.

Since the isoenzymes extracted from the organs are not identical with the corresponding isoenzymes in the serum and, therefore, display a different precipitation behaviour with regard to wheat germ lectin and since for the enrichment from serum insufficiently large amounts are available, it is an object of the present invention to provide a standard solution for use in the differentiated determination of alkaline phosphatase.

SUMMARY OF THE INVENTION

This problem is solved by the use of alkaline phosphatase to which is covalently bound a carbohydrate of the general formula I:

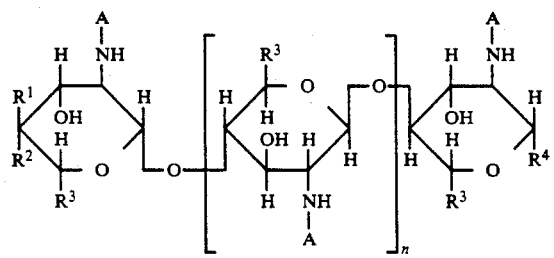

wherein n is 0, 1, 2 or 3, A is an acyl radical containing 2 to 5 carbon atoms, $R^1$ and $R^2$ are each hydrogen atoms or hydroxyl groups, $R^3$ is —COOH or —CH$_2$OH and $R^4$ is a hydroxyl group or a —CHOH—CHOH—CH$_2$OH or —NH—CO—CH$_2$—CH(NH$_2$)COOH radical or a complex containing a carbohydrate of general formula (I), as standard for the determination of human alkaline phosphatase.

In the case of the use of the derivatized phosphatase provided by the present invention, it is possible to imitate the precipitation behaviour of the alkaline bone phosphatase occurring in the serum, without losses of activity resulting.

DETAILED DISCLOSURE

According to the present invention, an alkaline phosphatase is used which cannot be precipitated with wheat germ lectin. For this purpose, there are especially preferred animal phosphatases, as well as the alkaline phosphatase from the human placenta. Preferably, there is used the isoenzyme from calf intestines or from human placenta.

This non-precipitatable alkaline phosphatase is then derivatized with a carbohydrate of the above-given general formula (I), compounds preferably being used in which A is an acetyl radical.

This carbohydrate is covalently bound to the alkaline phosphatase and provides for the selective precipitatability with wheat germ lectin.

For the derivatization of the phosphatase, there can be used a compound of general formula (I). It is also possible to use protein-polysaccharide complexes or polysaccharides which contain a structure according to general formula (I). Thus, complexes can be used which consist of compounds of general formula (I) to the hydroxyl groups of which are bound further sugars or proteins.

As carbohydrate, it is preferred to use chitotriose (also called tri-(N-acetylglucosamine), chitobiose (also called di-(N-acetylglucosamine) or a trisaccharide of two molecules of N-acetylglucosamine and one molecule of N-acetylneuraminic acid or -neuraminose. Also preferred is the glycoprotein ovomucoid obtained from egg white. It is especially preferred to use chitotriose or ovomucoid.

The carbohydrate is covalently bound to the alkaline phosphatase. Processes for the covalent bonding of polysaccharides to proteins or for the covalent bonding of proteins with proteins are known and appropriate processes are familiar to the expert. As a rule, a carbohydrate is activated by a chemical reaction, whereby a chemical bonding to amino, hydroxyl or carboxyl groups of proteins is made possible. Such activations are known to the expert and are described, for example, in Advances in Carbohydrate Chemistry and Biochemistry, pub. Academic Press, 37, 225–281/1980. Instead thereof, there can be used reactive groups of carbohydrates, for example amino groups or carboxyl groups which have possibly been previously introduced into the carbohydrate, in order chemically to link these with reactive groups of proteins with the addition of bifunctional reagents. Such bifunctional reagents include, for example, the cross-linking reagents described, for example, in the catalogue of Pierce Chemical Company (NL) (1987), pp. 311–349. As bifunctional groups, there are preferred homobifunctional compounds, such as imido esters or N-hydroxysuccinimide esters or heterobifunctional compounds which contain at least one N-hydroxysuccinimide ester, -sulphhydryl, -maleinimide, -pyridyldisulphide or -halo group. Glutardialdehyde can also be used.

For the precipitation of the derivatized isoenzyme according to the present invention, there is used a solution of wheat germ lectin. The precipitation behaviour of the phosphatase depends upon the number and the affinity of the binding points on the phosphatase and wheat germ lectin. Therefore, the particularly most favourable concentration of wheat germ lectin is, in each case, determined dependent upon the derivative of the phosphatase used.

The derivatized alkaline phosphatases according to the present invention can be used very advantageously as standards for the determination of alkaline bone phosphatase in the presence of alkaline liver phosphatase. The standard solutions are thereby prepared in known manner and used for the determination process. As a rule, the determination of the alkaline phosphatase takes place via the colour change of substrates or by density determinations.

The following examples are given for the purpose of illustrating the present invention:

EXAMPLE 1

There was prepared an alkaline phosphatase cross-linked with ovomucoid. For this purpose, 20 ml. of a solution of 200 mg. Type III-0 chicken egg white purified ovomucoid with a molecular weight of about 28,000 (T 2011 Sigma) were mixed in double distilled water with 10 ml. calf intestine AP containing 100 mg. phosphatase with an activity of about 66 kU. A 25% glutardialdehyde solution was diluted 1:10 with a solution which contained 1 mole/liter triethanolamine (pH 7.0), 1 mMole/liter magnesium chloride and 0.1 mMole/liter zinc chloride. 3.0 ml. of this glutardialdehyde solution were added to the batch. The solution was then stirred for 6 hours at +4° C. and subsequently incubated for 18 hours at +4° C. The reaction was stopped by the addition of 0.6 ml. of a 1M lysine hydrochloride solution with a pH of 6.0. Subsequently, 600 mg. Ficoll 70 were added to the solution. The resultant solution was lyophilised for 24 hours, there being obtained about 3150 mg. of lyophilizate with an activity of 8.3 U/mg.

EXAMPLE 2

40 mg. N,N',N''-triacetylchitotriose (T 2144, Sigma) were dissolved in 1 ml. 0.8 mMole/liter acetate (pH 5.5) and cooled to +3° C. Subsequently, 13.3 mg. sodium periodate were added thereto and incubation carried out for 40 minutes at +3° C. After a further addition of 182 µl. ethylene glycol, the temperature was increased to 22° C. and incubation continued for 20 minutes. Subsequently, the pH value of the batch was adjusted to 8.8 with 1 mMole/liter carbonate/bicarbonate buffer solution (pH 9.8). Thereafter, 0.8 ml. of a 2.2 mg./ml. solution containing alkaline phosphatase was added portionwise thereto. The procedure was such that, after 30 minutes, 8 mg. of the N,N',N''-triacetylchitotriose oxidized with sodium periodate were added to the alkaline phosphatase. After the addition of 40 mg. of the oxidized chitotriose, the coupling was stopped. The pH value was kept at 8.8 with 1 mMole/liter carbonate/bicarbonate buffer (pH 9.8). The coupling took place at ambient temperature. Subsequently, the pH value of the batch was adjusted to 8.0 with 1 mMole/liter triethanolamine buffer (TRA) (pH 7.0). 13.3 mg. sodium cyanoborohydride and 532 µl. of a glycine solution (250 mg./ml.) were added thereto, the pH value being kept at 8.0 with TRA buffer. The reaction mixture was left to react for 15 minutes at ambient temperature, whereafter it was dialyzed overnight at +4° C. against 5 liters of 10 mM TRA (pH 7.6). Derivatized phosphatase was obtained with an activity yield of 64%.

EXAMPLE 3

Alkaline phosphatase was derivatized with ovomucoid according to the process described in Example 1. However, as phosphatase, there was used alkaline phosphatase from human placenta (P 3895, Sigma). The activity yield was 28%.

EXAMPLE 4

A phosphatase was derivatized as described in Example 1. However, as starting phosphatase, there was used an alkaline phosphatase from *Escherichia coli* (P 4151, Sigma). The activity yield was 37%.

EXAMPLE 5

The derivatized phosphatases obtained in the preceding examples were tested for their precipitatability with wheat germ lectin.

PRINCIPLE

A dilution series of wheat germ lectins (WGA) was prepared and thereafter the WGA mixed in each case 1+1 with modified calf intestine AP in a human serum matrix, the AP thereby precipitating out. It was centrifuged off and the remaining AP activity determined in the supernatant. These activities were referred to the residual activity with the lectin concentration of 0 mg./ml. By plotting the percentage values against the lectin concentration used, there can be produced a precipitation curve (see FIG. 1 of the accompanying drawings). The optimum lectin concentration has proved to be the concentration which gives about 20% residual activity (sample reading off).

REAGENTS

Buffer: 5 mM acetate buffer (pH 5.0).

AP sample: about 1000 U/liter (25° C.) modified calf intestine AP in tris buffer (pH 7.0), with 0.02 mM zinc chloride and 1 mM magnesium chloride and 1% bovine serum albumin.

The determination of the AP activity took place according to the BM-AP-Test (Boehringer Mannheim GmbH, Order No. 415278).

The following reaction provided the basis of the test:

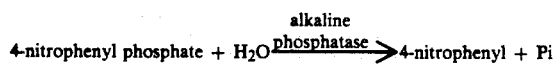

The increase of the absorption was measured at Hg 405 nm.

As reagents, there were used: diethanolamine buffer (1 mole/liter pH 9.8; magnesium chloride (0.5 mMole/liter); 4-nitrophenyl phosphate (0.67 mole/liter); 250 mg. disodium 4-nitrophenyl phosphate per liter of double distilled water.

3 ml. of buffer solution and 0.05 ml. of 4-nitrophenyl phosphate solution were mixed in a cuvette and incubated at a temperature of 37° C. The reaction was initiated by the addition of 0.05 ml. of sample. The increase of the absorption ($\Delta A$) per minute was measured, the linear part of the curve thereby being evaluated. For comparison, a blank value was determined in which case a magnesium chloride solution was used instead of the sample.

From the increase of the absorption ($\Delta A$), the volume activity can then be calculated according to the following equation:

$$\frac{3.10}{18.2 \times 0.05 \times 1} \times \Delta A/\text{min.} \ [\text{U/ml. of sample solution}]$$

CARRYING OUT

Dilution series: The lectin to be tested was diluted in acetate buffer to about 10 concentrations. The following concentrations have proved to be favourable: 0 mg./ml.; 0.1 mg./ml.; 0.5 mg./ml.; 1 mg./ml.; 2 mg./ml.; 3 mg./ml.; 4 mg./ml.; 5 mg./ml.; 7.5 mg./ml.; 10 mg./ml.; 20 mg./ml. and 30 mg./ml.

Precipitation: In each case, 0.1 ml. of the lectin dilutions was mixed with 0.1 ml. of the AP serum and incubated at 37° C. for 30 minutes. Thereafter, the mixtures were centrifuged for about 2 minutes and the supernatant further used.

AP determination: In the supernatants, the AP activity was determined with the optimized AP test at 25° C. according to the working instructions.

Evaluation: The measured activities were referred to the activity with the lectin concentration of 0 mg./ml. and given as percentage values. There followed a plotting of the residual activities as a function of lectin concentration used.

Result: FIG. 1 of the accompanying drawing shows the precipitation curves obtained for the alkaline phosphatase from calf intestines which had been modified according to Examples 1 to 4. The cross-linking with ovomucoid brought about outstanding precipitatabilities with low WGA concentrations, whereas all other processes provided AP's which only made possible a precipitation by the lectin with higher WGA concentrations.

Evaluation: It is to be the object of the purification either to obtain the smallest possible concentrations of WGA for 20% precipitation or so to optimize the conditions of the purification that 5 mg./ml. are always achieved.

We claim:

1. In a method for determination of human bone alkaline phosphatase in the presence of human liver alkaline phosphatase using a differential wheat germ lectin precipitation the improvement which comprises employing as a standard an alkaline phosphatase which cannot be precipitated with wheat germ lectin to which phosphatase is covalently bound an ovomucoid carbohydrate of the formula

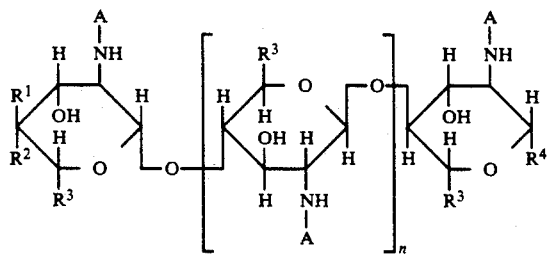

wherein n is 0, 1, 2 or 3, A is an acyl radical containing 2 to 5 carbon atoms, $R^1$ and $R^2$ are each hydrogen atoms or hydroxyl groups, $R^3$ is —COOH or —CH$_2$OH, $R^4$ is a hydroxyl group or a —CHOH—CHOH—CH$_2$OH or —NH—CO—CH$_2$—CH(NH$_2$)—COOH radical, or a complex containing said ovomucoid carbohydrate and wherein the binding provides for selective precipitability with wheat germ lectin to provide a standard compound for the determination of alkaline bone phosphate in the presence of alkaline liver phosphatase.

2. A method according to claim 1, wherein A is acetyl.

3. A method according to claim 1 wherein the carbohydrate is connected to the alkaline phosphatase via a bifunctional compound 4. A method according to claim 3, wherein the bifunctional compound is a homobifunctional imido ester or N-hydroxy-succinimide ester.

5. A method according to claim 3, wherein the bifunctional compound is glutardialdehyde.

6. A method according to claim 3 wherein the bifunctional compound is a heterobifunctional compound which contains at least one functional chemical group selected from the group consisting of N-hydroxysuccinimide, sulphhydryl, maleinamide, pyridylsulphide and halogen.

7. A method according to claim 1, wherein the alkaline phosphatase employed is obtained from calf intestine or from human placenta.

* * * * *